(12) United States Patent
Thundat et al.

(10) Patent No.: US 6,289,717 B1
(45) Date of Patent: Sep. 18, 2001

(54) MICROMECHANICAL ANTIBODY SENSOR

(75) Inventors: Thomas G. Thundat, Knoxville; K. Bruce Jacobson, Oak Ridge; Mitchel J. Doktycz, Knoxville; Stephen J. Kennel, Oak Ridge; Robert J. Warmack, Knoxville, all of TN (US)

(73) Assignee: U. T. Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/281,032

(22) Filed: Mar. 30, 1999

(51) Int. Cl.[7] .................. G01N 19/10; G01N 29/02; G01N 31/16

(52) U.S. Cl. ............... 73/23.2; 73/24.06; 422/82.01; 422/68.1; 436/163

(58) Field of Search .................. 73/23.2, 24.06, 73/53.01, 61.41; 422/82.01, 68.1; 436/163, 526, 147, 34

(56) References Cited

U.S. PATENT DOCUMENTS

| | | |
|---|---|---|
| Re. 35,544 | 7/1997 | Snow . |
| 4,236,893 | 12/1980 | Rice . |
| 4,242,096 | 12/1980 | Oliveira et al. . |
| 4,596,697 | 6/1986 | Ballato . |
| 4,637,987 | 1/1987 | Minten et al. . |
| 4,735,906 | 4/1988 | Bastiaans . |
| 4,847,193 | 7/1989 | Richards et al. . |
| 4,905,701 | 3/1990 | Cornelius . |
| 4,906,840 | 3/1990 | Zdeblick et al. . |
| 4,999,284 | 3/1991 | Ward et al. . |

(List continued on next page.)

FOREIGN PATENT DOCUMENTS

| | | | |
|---|---|---|---|
| 0 711 410 | * 1/1995 | (EP) | G01N/25/36 |
| WO 97/1697 | 5/1997 | (WO) . | |
| WO 98/50773 | 11/1998 | (WO) . | |

OTHER PUBLICATIONS

Gimzewski et al, Chem Phys Lett, 1994 V217,N5–6 (Jan. 28), P589–594.*

Photothermal Spectroscopy with Femtojoule Sensitivity Using a Micromechanical Device, J.R. Barnes et al., *Letter to Nature*, vol. 372, Nov. 3, 1994, pp. 79–81.

Uncooled Thermal Imaging using a Piezoresisitive microcantilever, P.I. Oden, et al., *American Institute of Physics*, Let. 69 (21), Nov. 18, 1996, pp. 3277–3279.

Viscous Drag Measurements Utilizing Microfabricated Cantilevers, P.I. Oden, et al., *Appl. Phys. Lett.* 68 (26), Jun. 24, 1996, pp. 3814–3816.

Microcantilever Sensors, T. Thundat, et al., *Microscale Thermophysical Engineering*, 1:185–199, 1997.

(List continued on next page.)

*Primary Examiner*—Hezron Williams
*Assistant Examiner*—Jay L. Politzer
(74) *Attorney, Agent, or Firm*—J. Herbert O'Toole; Hardaway/Mann IP Group

(57) ABSTRACT

A sensor apparatus is provided using a microcantilevered spring element having a coating of a detector molecule such as an antibody or antigen. A sample containing a target molecule or substrate is provided to the coating. The spring element bends in response to the stress induced by the binding which occurs between the detector and target molecules. Deflections of the cantilever are detected by a variety of detection techniques. The microcantilever may be approximately 1 to 200 μm long, approximately 1 to 50 μm wide, and approximately 0.3 to 3.0 μm thick. A sensitivity for detection of deflections is in the range of 0.01 nanometers.

14 Claims, 2 Drawing Sheets

U.S. PATENT DOCUMENTS

| | | |
|---|---|---|
| 5,001,053 | 3/1991 | Takahashi et al. . |
| 5,130,257 | 7/1992 | Baer et al. . |
| 5,135,852 | 8/1992 | Ebersole et al. . |
| 5,156,972 | 10/1992 | Issachar . |
| 5,179,028 | 1/1993 | Vali et al. . |
| 5,221,415 | 6/1993 | Albrecht et al. . |
| 5,283,037 | 2/1994 | Baer et al. . |
| 5,306,644 | 4/1994 | Myerholtz et al. . |
| 5,323,636 | 6/1994 | McGowan et al. . |
| 5,339,675 | 8/1994 | DiLeo et al. . |
| 5,445,008 | 8/1995 | Wachter et al. . |
| 5,445,970 | 8/1995 | Rohr . |
| 5,445,971 | 8/1995 | Rohr . |
| 5,477,716 | 12/1995 | Snow . |
| 5,482,678 | 1/1996 | Sittler . |
| 5,494,639 | 2/1996 | Grzegorzewski . |
| 5,501,986 | 3/1996 | Ward et al. . |
| 5,552,274 | 9/1996 | Oyama et al. . |
| 5,595,908 | 1/1997 | Fawcett et al. . |
| 5,658,732 | 8/1997 | Ebersole et al. . |
| 5,705,399 | 1/1998 | Larue . |
| 5,719,324 | 2/1998 | Thundat et al. . |
| 5,807,758 * | 9/1998 | Lee et al. ............................ 436/526 |
| 6,016,686 * | 1/2000 | Thundat ............................... 73/23.2 |
| 6,096,559 * | 8/2000 | Thundat et al. ...................... 436/147 |

OTHER PUBLICATIONS

NanoSensor Array Chips, T. Thundat, et al., *Appliance Manufacturer*, Apr. 1997, pp. 57–58.

Microfabrication of Cantilever Styli for the Atomic Force Microscope, T. R. Albrecht et al., *J. Vac. Sci. Technol.* A 8 (4) Jul./Aug. 1990, pp. 3386–3396.

A Nondestructive Method for Determining the Spring Constant Cantilevers for Scanning Force Microscopy, J.P. Cleveland et al., *Rev. Sci. Instrum.* 64(2), Feb. 1993, pp. 403–417.

A Mechnical Nanosensor in the Gigahertz Range: Where Mechanics Meets Electronics, V.T. Binh, et al., *Surface Science Letters*, 301, 1994, pp. L225–L228.

Sensing Discrete Streptavidin–Biotin Interactions with Atomic Force Microscopy, G.U. Lee et al., *American Chemical Society*, vol. 10, No. 2, 1994, pp. 354–357.

Observation of a Chemical Reaction Using a Micromechanical Sensor, J.K. Gimzewski et al., *Chemical Physics Letters*, vol. 217, No. 5.6, Jan. 28, 1994, pp. 589–594.

Detection of Mercury Vapor Using Resonating Microcantilevers, T. Thundat, et al., *Appl. Phys. Lett.* 66 (13), Mar. 27, 1995, pp. 1695–1697.

A High–Sensitivity Micromachined Biosenson—David R. Baselt, Gil U Lee, Darolyn M. Hansen, Linda A. Chrisey, and Richard J. Colton pp. 672–680.

* cited by examiner

MICROMECHANICAL ANTIBODY SENSOR

CROSS-REFERENCE TO RELATED APPLICATIONS

The invention relates to U.S. patent application Ser. No. 09/039,707, filed Mar. 16, 1998 entitled "Micromechanical Calorimetric Sensor" and to U.S. patent application Ser. No. 09/042,601, filed Mar. 16, 1998 entitled, "Micromechanical Potentiometric Sensors" the specifications of which are incorporated herein by reference.

STATEMENT AS TO RIGHTS TO INVENTIONS MADE UNDER FEDERALLY-SPONSORED RESEARCH AND DEVELOPMENT

The United States Government has certain rights in this invention pursuant to contracts number DE-AC05-96OR22464 and DE-AC05-84OR21400, between the U.S. Department of Energy and Lockheed Martin Energy Research Corporation.

BRIEF SUMMARY OF THE INVENTION

This invention relates to novel methods for the detection of biological and biologically derived materials using micromechanical devices as the detection mechanism. The measurement of small changes in the deflection of a micromechanical device such as a cantilever spring element which has been coated with one member of a specific binding partner provides qualitative and quantitative determination of the presence of the other specific binding partner. A specific binding partner is a member of a pair of biochemical entities which exhibit specific binding, i.e., a high intrinsic affinity or high total avidity (q.v. Kabat, E. A., Structural Concepts in Immunology and Immuno Chemistry, $2^{nd}$ ed. New York; Holt Rinehart & Winston, 1976). Non-limiting examples are Ag-Ab (Antigen-Antibody) complexes, nucleic acid probes and targets, steroid hormone-peptide binding pairs, etc.

BACKGROUND OF THE INVENTION

Microcantilevers can be utilized in biophysical and biochemical studies to determine energy changes as indications of biochemical reactions in a medium. There is a great interest in developing ultra-miniature probes and assays that require very small volumes of sampled media for accurate qualitative and quantitative analysis of biochemical reactions and these assays can be performed using a microcantilever bound substrate.

In Thundat et al., U.S. Pat. No. 5,719,324, a piezoelectric transducer is disclosed that is fabricated with a cantilever having a spring element treated with a chemical which reacts with a specific vapor phase chemical. An oscillator means maintains a resonant vibrational frequency during detection of a chemical, with changes in resonant frequency indicating amounts of targeted chemical detected in the monitored atmosphere. Alternatively, the rate of cantilever bending is monitored to indicate the target chemical concentration.

In Wachter et al., U.S. Pat. No. 5,445,008, a mass microsensor is disclosed that is fabricated with a microcantilever that oscillates due to a piezoelectric transducer, with a chemical coating on the microcantilever that absorbs a targeted chemical from the monitored atmosphere. The resonant frequency of the microcantilever is analyzed to determine changes that indicate amounts of targeted chemical detected in the monitored atmosphere.

In Marcus et al., U.S. Pat. No. 5,475,318, a microprobe is disclosed that includes a microcantilever, a base, a probe tip projecting from the base, and a heating element that heats the probe tip, which comes into contact with a material to be investigated.

In Hafeman, U.S. Pat. No. 4,963,815, a device and method is provided for determining an analyte by measuring a redox potential-modulated photoinducing electrical signal from an electronically conducting layer on a semiconductor device.

In Kolesar, U.S. Pat. No. 4,549,427, a chemical nerve agent detector is disclosed that includes a transducer having two microcantilever oscillators. The active microcantilever of the two microcantilevers has a chemically selective substance that absorbs chemical nerve agents from the atmosphere, with modifications in the oscillation of the active microcantilever, and comparisons are made between the frequency of the active cantilever and the reference cantilever.

The above described methods and devices of measuring chemical and micromechanical parameters are not directed towards immunoassays which can detect the binding of a few molecules upon a substrate. The present invention describes a novel and sensitive technique which measures adsorption-induced forces for detecting proteins, other biopolymers, nucleic acid sequences, and micro-organisms in a gas or liquid medium using microcantilever.

SUMMARY OF THE INVENTION

It is an object of this invention to provide a detection and quantitation method for antibody-antigen binding reactions which are capable of detecting low levels of chemical binding.

It is a further object of this invention to provide a microcantilever assay for the detection of reactions involving biomolecules coupled to the microcantilever which results in a stress-induced bending of the cantilever.

It is an additional object of this invention to provide an ultra-miniature assay template which requires reduced sample volumes for operation.

It is a further and more particular object of this invention to provide an ultra-miniature microcantilever that provides a sensitivity sufficient to detect a single microorganism from a sample.

These and other objects of the invention are accomplished by an apparatus and a method for detecting and measuring highly specific binding reactions in a sampled media. The present invention provides a cantilever with one of its surfaces coated with specific binding partners such as antibody or antigen molecules, or with specific binding peptides identified from display libraries, while the other surface is covered with a different, possibly inert, material. As long as the amount of adsorption is different on the opposing surfaces, or there are different interactions of monitored molecules on opposing surfaces, there will be a differential stress. Since the cantilever thickness is very small, an antibody-antigen (Ab-Ag) type of interaction is manifested as changes in the differential surface stress of the microcantilever surface. This surface stress, for example, can originate from changes in volume, or charge,or polarization, or induced polarization due to the formation of chemical interactions. If a specific interaction does not take place, there will not be any change in surface stress when compared to a reference microcantilever. These changes in differential surface stress manifest themselves as changes in cantilever deflection which can be measured with a sub-angstrom sensitivity. The cantilever technique offers more simplicity and higher sensitivity than any currently used techniques.

Upon interaction with specific agents a stress is induced which deflects the spring element. The apparatus and the method provides a means for detection of the changes in deflection of the cantilevered spring element created by the physical binding or biochemical interaction stress. The deflection is measured and provides a basis for quantitative and qualitative analysis. The microcantilever assays provide sensitivities in the sub-nanometer range for deflections in response to stresses on the spring element.

BRIEF DESCRIPTION OF THE DRAWINGS

The invention's features and advantage will become apparent from a reading of the following detailed description, given with reference to the various figure of drawing, in which.

DETAILED DESCRIPTION OF THE PREFERRED EMBODIMENT

In accordance with this invention, it has been found that a detection method and apparatus can be provided which is extremely sensitive to slight changes in the structural stress associated with a chemical binding to a microcantilever-bound substrate. The invention is capable of measuring deflection in the microcantilever spring element brought about by the specific chemical binding. The invention utilizes a biomaterial coating such as a polyclonal or monoclonal antibody, an antigen, a nucleic acid sequence, a lectin or other molecule which has a highly specific affinity for a target molecule. A method of detecting and quantifying the specific interactions by measuring the movement of a microcantilever spring element is disclosed. The movement of the microcantilever spring element is detected using a detection means that provide detection sensitivities in the sub-nanometer range for deflection measurements. The small size of the spring element and the high sensitivity of the detection means allow very small samples to be tested.

In accordance with FIGS. 1–4, preferred embodiments for the present invention is a sensor apparatus 1 comprising a base 2 having at least one microcantilever spring element 3 (also referenced as a microcantilever), with or without a separate reference microcantilever spring element 15. Spring element 3 may have the dimensions of approximately 1.0 to approximately 200 $\mu$m long, approximately 1.0 to 50 $\mu$m wide, and approximately 0.1 $\mu$m to 3.0 $\mu$m thick. The alternate dimensions are approximately 50 $\mu$m to approximately 200 $\mu$m long, approximately 10 $\mu$m to approximately 30 $\mu$m wide, and approximately 0.3 $\mu$m to approximately 3.0 $\mu$m in thickness.

Each of the above dimensions may be varied to configure the spring element 3 in a variety of desired shapes. The size and shape of the spring elements are not a critical limitation.

Figure 1:
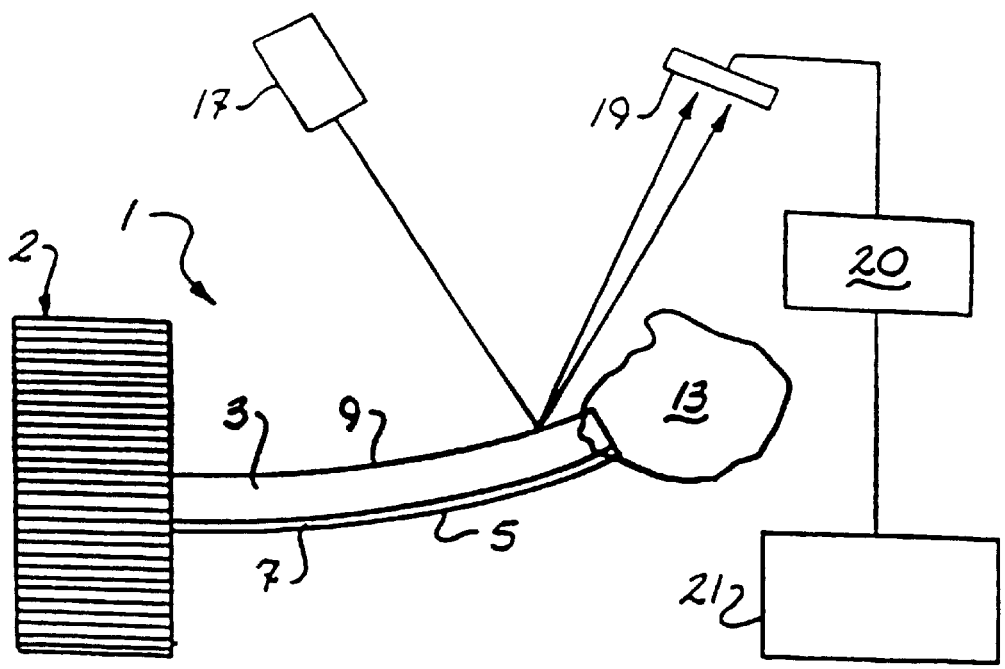
FIG. 1 is a pictorial schematic of a first embodiment of the microcantilever assembly and bending detection assembly of the present invention.
Figure 2:
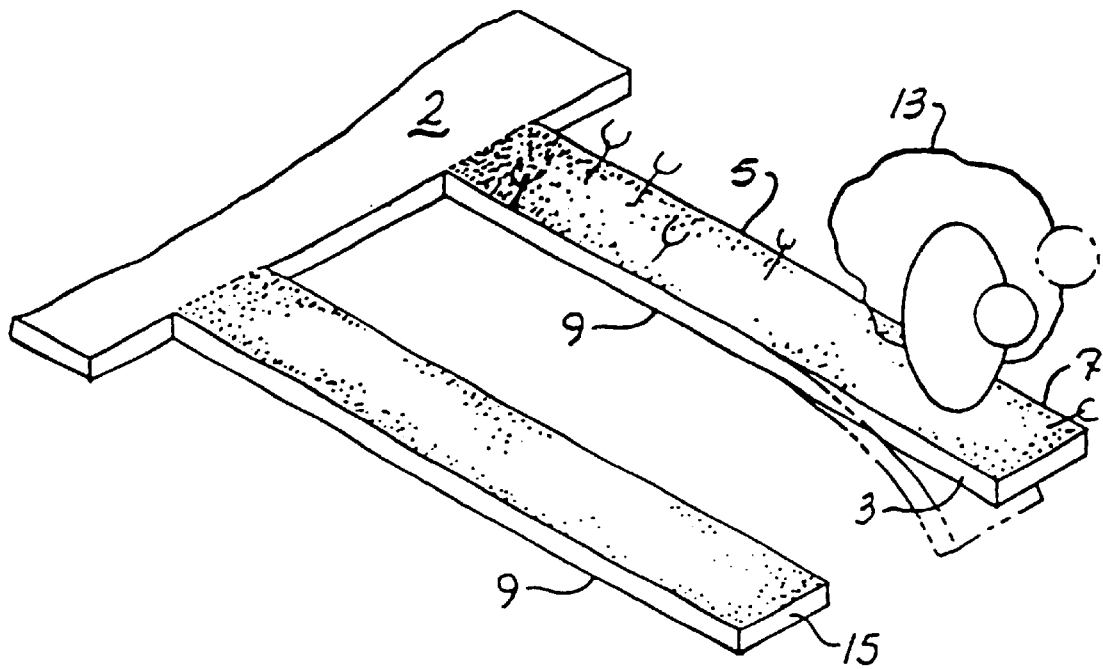
FIG. 2 is a perspective view of the present invention having a sample in contact with the microcantilever.
Figure 3:
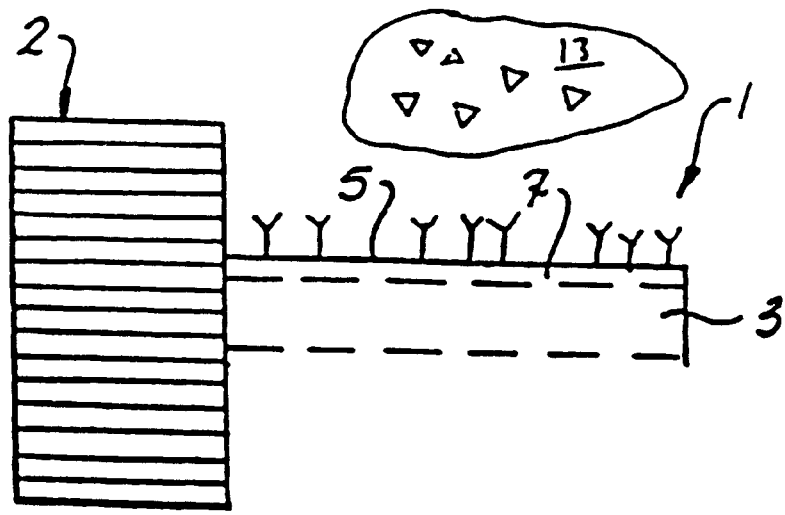
FIG. 3 is a cross-sectional side view of one alternate embodiment of the present invention having two coated surfaces.
Figure 4:
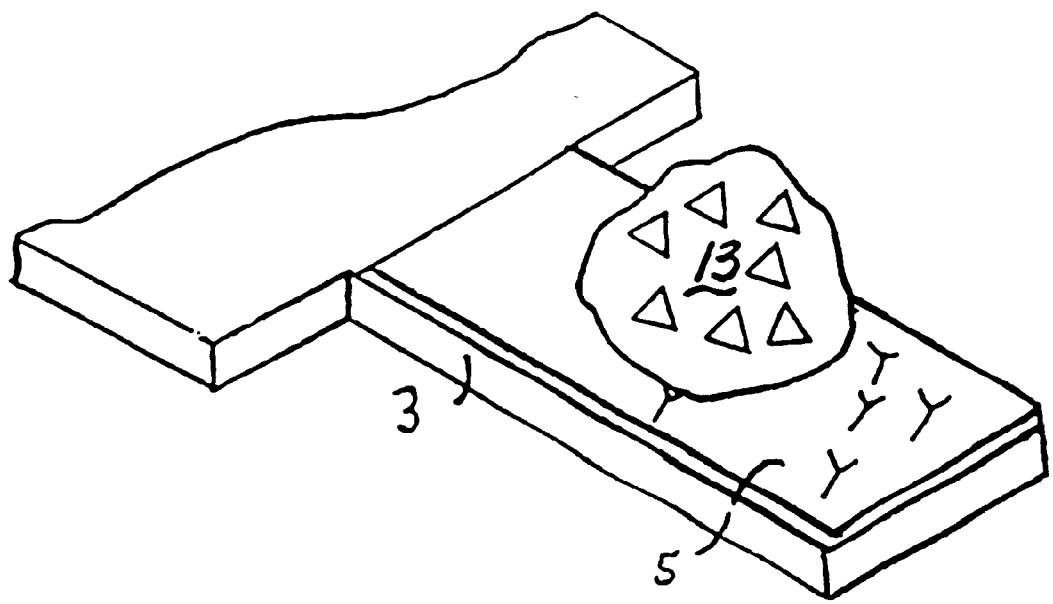
FIG. 4 is a side perspective view of one alternate embodiment of the present invention having a coated region at the distal end of the microcantilever.

Spring element 3 extends outward from the base 2 as shown in FIG. 1. The sensor apparatus 1 may consist of a plurality of microcantilever spring elements 3 attached to the sensor apparatus 1. Reference microcantilever 15, if utilized, is located in close proximity to spring element 3. Each microcantilever is preferably constructed of materials such as silicon or silicon oxide which provides a useful substrate for the attachment of an antibody. While microcantilevers can be provided from a variety of materials, the present invention benefits from materials which will facilitate binding of an antibody (coating) and responds (deflects) in response to subsequent antibody-antigen binding.

ELISA techniques for coating glass using various linkers are applicable to silicon. The linker chosen is selected from that compatible with the detector molecule used. Linkers such as poly-L-lysine are preferred which also serve as stress transducers.

Spring element 3 may be approximately rectangular in crosssection as shown in FIGS. 1–5. Surface 5 may be provided by a coating of "detector" molecules, i.e., one member of a binding pair. The coated region 5 may be located at varied locations and sizes and the coating may be placed on either surface 7 or 9 provided that the coating is on one or the other side.

The spring constant of microcantilever spring element 3 is designed to produce cantilever deflection at the nanometer level. The low spring constant of the spring element 3 having coating 5 allows the spring element to deflect in response to binding of a target molecule to the detector molecule during reactions which occur when sample 13 is placed on one side of the spring element 3, or having a difference in the number of molecules adsorbed on one side as compared to the other side.

The surface coating 5 may include enzymes, peptides, proteins, polysaccharides, nucleic acids, carbohydrates, antibody or antigen molecules, pharmacological agents (i.e. drugs, including small organic molecules such as aspirin), and other biopolymers, and any class of biochemical compounds which react with one or more analytes or other biopolymers in a sample 13 placed on the coating 5. The chemical reactions of one or more biomolecules in sample 13 produce a stress-induced deflection to the spring element 3.

The stress induced deflections may be brought about by volume changes due to the formation of chemical interactions. In addition, the present assay is extremely sensitive to absorption-induced forces. As a result, the system is well-suited for detecting proteins, other biopolymers, and microorganisms in a gas or liquid medium using the miniature nature of a microcantilever.

These microcantilevers have a response time in the range of microseconds to milliseconds. Since the cantilever thickness is very small, an antibody-antigen type of interaction maybe manifested as changes in the differential surface stress. If the specific interaction does not take place, there will not be any change, when compared to control values, in surface stress. These changes in differential surface stress manifest themselves as changes in cantilever deflection which can be measured with a sub-angstrom sensitivity. The cantilever technique offers more simplicity and higher sensitivity than any currently used techniques.

Responses to forces as small as approximately a few pico Newtons are possible for the microcantilevers of the present invention, providing an advantage in sensitivity over prior calorimeter devices. Microcantilevers with force constants as small as 0.08 Newton/meter are commercially available from Park Instruments, Sunnyvale, Calif. Most commercial micro cantilevers are silicon based, but other materials such as GaAs are also useful.

As the detector molecules on the first surface 5 undergo interactions with target molecules present in sample 13, the resulting reactions result in a structural change in the shape of spring 3 caused by a change in surface stress. The bending of the microcantilever 3, even though extremely small, can be detected by known laser optical techniques with sub-nanometer sensitivities. If laser detection is used, at least one layer on one surface, or one end of a surface of sensing microcantilever 3, must be reflective of laser light. The laser optical sensing means includes a photo diode generator 17 of laser light focused on the first surface 7 or the second surface 9 of sensor microcantilever 3, with a photodetector 19 positioned to receive the reflected laser light, with analysis of the bending of the sensing microcantilever 3 by microprocessors.

Alternative detection means are possible. These include a piezoresistive detection means, a piezoelectric detection means, a capacitive detection means, and an electron tunneling detection means, all of which are conventionally known. Each detection means determines changes in deflection of the microcantilever 3 with sensitivities comparable to the sub-nanometer sensitivity of the laser sensing means. A general discussion of deflection detection techniques is provided in Gimzewski et al. ("Observation of a chemical reaction using a micromechanical sensor," 217 *Chem. Phys. Lett.* 589, at 593 (1994)) which is incorporated herein by reference.

For a monolayer coating, the extent of bending is directly proportional to the amount of target molecule which binds to the sensor. The confinement of the antibody-antigen type of interaction to one side of the cantilever causes a tangential stress in the whole cantilever. One of the unique characteristics of microcantilevers is that they can be made to undergo bending due to changes in differential surface stress by confining the adsorption to one side of the thin cantilever. Using Stoney's formula, the radius of curvature of bending of the cantilever due to adsorption can be written as:

$$\frac{1}{R} = \frac{6(1-v)}{Et^2} \delta s \quad (1)$$

where R is the radius of curvature for the cantilever, v and E are Poisson's ratio and Young's modulus for the substrate respectively, t is the thickness of the cantilever and $\delta s$ is the film stress. The radius of curvature due to bending of a cantilever is given by, $$\frac{1}{R} = \frac{2z}{L^2} \quad (2)$$

where z is the displacement at the unsupported end of the cantilever and L is the length of the cantilever beam. Using (1) and (2), a relationship between the cantilever displacement and the differential surface stress is obtained:

$$z = \frac{3L^2(1-v)}{Et^2} \delta s \quad (3)$$

This bending can be measured with a sub-nanometer resolution by reflecting a light from a diode laser at the end of a cantilever into a position sensitive detector.

The technique described here is a d.c. technique. If the cantilever is coated with or comprises a stress-sensitive material, the stiffness can be changed by bending the cantilever. The stress-sensitive material may preferably be selected from, but not limited to, the group consisting of metals, metal alloys, dielectric materials, polymeric materials and combinations thereof. Specific examples of such polymeric materials include, but are not limited to, such polymers as polycarbonate of bisphenol, poly[N,N'-(p,p'-oxydiphenylene)pyromellitimide], poly (vinyl chloride), and the like. Many other polymers are known to the skilled artisan which perform as described herein.

Another way to affect the spring constant of the cantilever is by using a non-uniform force field. For example, the cantilever can be placed in a nonuniform electric field. When the cantilever bends the spring constant varies as a function of bending resulting in different resonance frequency. This, however, can be made into a.c. technique by coating the inert side of the cantilever with a stress sensitive film. Differential stress can cause resonance frequency shift. Thundat U.S. Pat. No. 5,719,324, the change in resonance frequency can be amplified by applying a stress sensitive film on one side. The bending of the cantilever can now be converted into an a.c. signal by detecting the variation in resonance frequency of the cantilever. As the cantilever bends, the stiffness of the cantilever changes due to the stress within the sensitive film. The small amplitude resonance frequency of the cantilever varies as the cantilever bends. Therefore, the d.c. variation in cantilever bending can be converted into the a.c. signal.

It is also known that the stress-induced changes in spring constant, $\delta k$, of the cantilever can be calculated from the bending of the cantilever, $$\delta K = \frac{\pi 2n(\delta s1 - \delta s2)}{4n_1} \quad (4)$$

where $\delta s_1$ and $\delta s_2$ are the differential stress on the cantilever surfaces and $n_1$ is a geometrical constant. The resonance frequency of the cantilever changes due to changes in resonance frequency caused by static bending of the cantilever.

The bending of the spring element 3 can be measured in comparison to an untreated reference microcantilever 15. Plotting the bending of the untreated reference microcantilever 15 as a function of deflection between spring element 3 and microcantilever 15 will provide peaks corresponding to the desorption of the analyte from the coating 5 of spring element 3.

Method of Detecting and Measuring

The steps of detecting and measuring structural changes within a sensor which corresponds to reactions between target molecules in a sample of monitored media and detector molecules carried on a sensor surface include: providing a base; attaching at least one cantilevered spring element to the base; coating at least one surface on the spring element with a substance which is or may be attached to a detector molecule; exposing the coated region to a liquid or aerosol sample; deflecting the spring element in proportion to the number or concentration of target molecules which bind to the detector molecules; and detecting the deflection by a detector comprising a laser light source directing light at the cantilevered spring element surface. The reflected light from the cantilever surface is captured by a light detector near the cantilevered spring element, the detector receiving reflected light from the cantilever surface before, during, and after bending of the microcantilever. The degree of bending is measured in reference to a neutral position of the cantilever, or a control microcantilever, and a microprocessor is provided for analyzing deflection information from the measuring steps. The changes in deflection are compensated for deflection observed in controls. Control microcantilevers can determine the impact of non-specific binding by target molecules, deflection resulting from temperature changes, pH changes, and other environmental changes which may affect spring element 3. Well known microprocessors and mathematical formulas are used to calculate the deflection changes as a function of specific target and detector molecular binding.

Additional Embodiments

In accordance with illustrations used to depict Ag-Ab interactions, the coating 5 carries one binding partner indicated by a "y" and the analyte in the sample is shown as a "delta."

EXAMPLE 1

A microcantilever sensor can be provided for determining the level of antigen present in a liquid sample. As seen in FIG. 1, an antibody layer 5 can be provided on the surface of spring element 3. preferably on one surface only. Binding molecules may be used to make antibody coating uniform and make accessible to antigen. Layer 5 can comprise a polyclonal antibody, a monoclonal antibody, or a mixture of different polyclonal antibodies directed to a common target molecule. The antibodies are conjugated to element 3 as represented by layer 5.

Following standard blocking protocols using bovine serum albumin (BSA) to reduce nonspecific binding interactions (other proteins, detergents, etc., can be used as well), a solution containing a possible analyte or target molecule is used to incubate layer 5 using temperatures, pH values, time intervals and buffers as are well known within the art of immunoassays. While a standard incubation time of 30 minutes is typical for an ELISA protocol, the sensitivity of the present sensor will enable measurable reactions to occur in a matter of seconds.

The deflection of the spring element 3, compared to a control sensor having no target molecules, will indicate the presence of the antigen. Quantification of the target molecule concentration can occur by comparison to controls using a dilution series having a known quantity of the antigen target.

The rapid reaction time of the sensor enables a rapid screening protocol for qualitative measurements. For instance, rapid screening of monoclonal antibodies can be conducted by using the antigen (or immunogen) as the detector molecule(s) in layer 5. Serum derived from monoclonal producing hybridoma cell cultures can be introduced to the sensor as described above. A positive reaction indicates a specific binding which warrants further investigation of the tested hybridoma line. Since thousands of cell lines may need to be tested per fusion, of which the vast majority produce no antibody of interest, the present sensor offers the ability to greatly streamline the screening process.

Further, the small size of the sensor requires only minute concentrations of antigen to be used as the detecting molecule. This ability may be essential to allow screening protocols to be developed for antigens or like detector molecules which are only available in limited supply.

A further advantage of the present sensor is that the direct interaction between molecules is measured. Unlike many traditional immunoassays, a separate "visualization" step requiring additional incubation steps is not needed. This results in increased time savings and avoids the need for additional reagents. Because of the binding between partners is reversible, it may be feasible to reverse the detection system, although disposable sensors are more likely for clinical uses such as serum assays.

EXAMPLE 2

The current sensor system is also useful as a detector and/or isolator of single living cells from a liquid sample. The dimensions of the microcantilever spring element 3 are such that a single procaryotic cell (1–10 $\mu$m in length) such as a bacterium, or a single eucaryotic cell (10–100 $\mu$m in length) can be bound to the sensor layer. Given the large size of any living cell, compared to the size of the cantilever, a single cell will result in a significant and measurable deflection of the cantilever spring element 3.

Accordingly, a sensor can be provided to detect a target species of bacterium using either a lectin or antibody in layer 5 which is specific for the bacterium of interest. For instance, a detector for coliform bacteria, an indicator of fecal or sewage contamination, can be provided to monitor water quality in wells, lakes, or pools.

In summary, the present invention describes a novel and extremely sensitive technique to measure the often overlooked occurrence of adsorption-induced forces for detecting proteins, other biopolymers, and micro-organisms in a gas or liquid medium using the miniature nature of a microcantilever. These microcantilevers have a response time in the range of microseconds to milliseconds. Since the cantilever thickness is very small, the antibody-antigen type of interaction is manifested as changes in the differential surface stress and no additional reagents or steps are required. If specific interactions do not take place, there will not be any change in surface stress. These changes in differential surface stress manifest themselves as changes in cantilever deflection which can be measured with a sub-angstrom sensitivity. The cantilever technique offers more simplicity and higher sensitivity than any currently used techniques.

Many variations will undoubtedly become apparent to one skilled in the art upon a reading of the above specification with reference to the figures. As the foregoing description is exemplary in nature, the spirit and scope of the invention should be limited only by the spirit and scope of the following appended claims.

What is claimed is:

1. An apparatus for detecting specific binding partner molecules from a sample of monitored media containing one specific binding partner to be analyzed, comprising:
    a base;
    at least one cantilevered spring element attached to said base, said spring element comprising at least one surface having a coated region comprising at least one binding partner molecule specific to the partner to be analyzed; and
    a means for measuring an irreversible deflection of said spring element resulting from mechanical stresses established by the reaction of said binding partner molecules.

2. The apparatus according to claim 1, wherein at least one cantilevered spring element is composed of a material selected from the group consisting of ceramics, polymers, quartz, silicon nitride, silicon, silicon oxide, silicon nitride, aluminum oxide, tantalum pentoxide, germanium, germanium dioxide, gallium arsenide, and zinc oxide.

3. The apparatus according to claim 1 wherein at least one cantilevered spring element comprises a microcantilever, said microcantilever having a length of about 1 to about 200 µm, a width of about 1 to about 50 µm, and a thickness of about 0.3 to about 3.0 µm.

4. The apparatus according to claim 1 further comprising a reference cantilevered spring element in close proximity to said base, said reference cantilever having a length and a width corresponding to said detector microcantilever.

5. The apparatus according to claim 1, wherein said deflection measuring means has a sensitivity of less than about 0.01 nanometers of deflection.

6. The apparatus according to claim 1, wherein said deflection measuring means comprises one of a laser detecting means, a piezoresistive detecting means, a piezoelectric detecting means, a capacitive detecting means, and an electron tunneling detecting means.

7. The apparatus according to claim 6, wherein said deflection measuring means comprises:
   a reflective region on said spring element;
   a laser light source positioned to direct light at said reflective region of said spring element;
   a light sensitive detector positioned to receive reflected light from reflective region of said spring element; and
   a microprocessor for quantifying the deflection of said spring element.

8. The apparatus as described by claim 1, wherein said at least one cantilevered spring element further comprises:
   a plurality of cantilevered spring elements attached to said base, each of said spring elements comprising:
      a surface having at least one region coated with or attached to a detector molecule; and,
   a plurality of means for measuring deflections, each associated with a respective one of said plurality of cantilevered spring elements.

9. A method for detecting a specific binding partner molecule from a sample of monitored media containing one specific binding partner to be analyzed, comprising the steps of:
   providing at least one cantilevered spring element attached to a base and having a surface having a coated region comprising a plurality of binding partner molecules specific to the partner to be analyzed;
   exposing said coated region to a substrate containing a binding partner molecule, said binding partner molecules binding to said partner molecules, thereby providing a stress induced shape change to said spring element;
   measuring an irreversible deflection of said spring element; and
   quantifying said deflection of said spring element.

10. The method according to claim 9, wherein said step of providing a base comprising at least one cantilevered spring element further comprises providing a microcantilever having a length of about 1 to about 200 µm, a width of about 1 to about 50 µm, and a thickness of about 0.3 to about 3.0 µm.

11. The method according to claim 9, wherein said step of providing said deflection measuring means comprises:
   providing a reflective area on said spring element;
   providing a laser light source directing light at said reflective area;
   positioning a light sensitive detector to receive light from said reflective area;
   measuring reflected light from said reflective area;
   providing a microprocessor for analyzing information from said positioning step and said measuring step;
   estimating deflections of said spring element; and
   correlating said deflections of said spring element to known standards.

12. A method according to claim 9, wherein said plurality of specific binding partner molecules are coated upon said surface through an intermediate molecular bridge which acts as a stress transducer molecule.

13. A method according to claim 12 wherein said intermediate molecular bridge is poly-L-lysine.

14. A method according to claim 11 wherein said deflection of said spring element is correlated to a concentration of said specific binding partner to be analyzed.

* * * * *